United States Patent [19]

Quadro

[11] Patent Number: 5,604,254
[45] Date of Patent: Feb. 18, 1997

[54] INDOLE DERIVATIVE HAVING PROLONGED IMMUNOSTIMULATING ACTIVITY AND PHARMACEUTICAL COMPOSITIONS THEREFROM

[75] Inventor: Giuseppe Quadro, deceased, late of Novara, Italy, by Ettore Quadro, Laura Quadro, heirs

[73] Assignee: Yason S.r.l., Novara, Italy

[21] Appl. No.: 448,511

[22] PCT Filed: Nov. 27, 1992

[86] PCT No.: PCT/EP92/02737

§ 371 Date: Dec. 1, 1995

§ 102(e) Date: Dec. 1, 1995

[87] PCT Pub. No.: WO94/12475

PCT Pub. Date: Jun. 9, 1994

[51] Int. Cl.⁶ .................. A61K 31/40; C07D 209/04
[52] U.S. Cl. .................. 514/419; 548/491
[58] Field of Search ................ 548/491; 514/419

[56] References Cited

PUBLICATIONS

G. W. Bennett et al., J. Recept. Res. vol. 7, No. 1–4, pp. 555–579 1987.

R. Besselievre et al., Biomed. Express, vol. 33, No. 7, pp. 226–228 1980.

M. Strahilevitz et al., Biol. Psychiatr. vol. 3, pp. 27–236 1971.

I. D. Pletnev, Khim. Geterotsikl. Soedin., No. 1, pp. 76–80 1972.

P. N. Stefanescu, Chemical Abstracts, vol. 70, abst. No. 37594, p. 326 of Rev. Chim. (Bucharest), 19(8), pp. 444–447 1986.

*Primary Examiner*—Raymond Henley, III
*Attorney, Agent, or Firm*—Bucknam and Archer

[57] ABSTRACT

The compound N-[N'acetyl(glycinyl)]-5-methoxytryptamine, of formula (I)

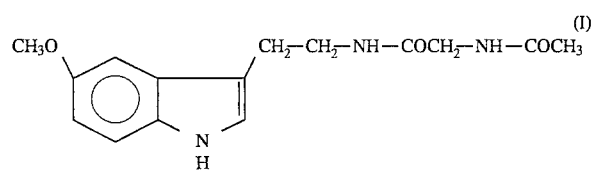

exhibited markedly prolonged immunostimulating activity. The method of preparation and the method of use are described.

5 Claims, No Drawings

INDOLE DERIVATIVE HAVING PROLONGED IMMUNOSTIMULATING ACTIVITY AND PHARMACEUTICAL COMPOSITIONS THEREFROM

This Application is a 371 of PCT/EP92102737 filed Nov. 27, 1992.

The present invention relates to an indole derivative having prolonged immunostimulating activity, namely N-[N'-acetyl(glycinyl)]-5-methoxytryptamine, of formula (I)

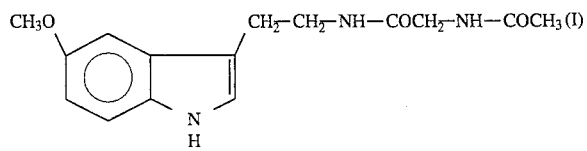

The immunomodulating and immunostimulating properties of 5-methoxytryptamine, or melatonin, have been evidenced in successive stages by G. J. M. Maestroni and A. Conti: in 1986 in normal rats, in 1987 on the primary anti-body response in the mouse, in 1988 in mice in which stress had been induced by a Vaccinia Virus injection; and by various Authors more recently. However, the therapeutic use of melatonin is limited as drug effective levels in blood stream can be attained for only short times, after acute administration.

Now it has surprisingly been found that compound (I) (which hereinafter will also be called YS-2051), besides having a higher membrane affinity, also allows to obtain markedly higher and more prolonged plasmatic concentrations after oral administration.

In fact, after administration of equimolar doses of YS-2051 and melatonin, the following advantages for YS-2051 were evidenced from the pharmacokinetic data of melatonin plasmatic concentrations:

Maximal concentration: +57% in case of YS-2051

Half-life time: +104% in case of YS-2051

Area under curve: +120% in case of YS-2051

The invention also relates to a process for the preparation of YS-2051, characterized in that 5methoxytryptamine (II) is reacted with a N-acetylglycine reactive derivative, of formula (III), according to scheme

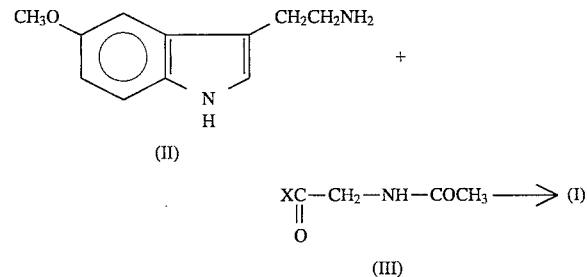

wherein X is a halogen atom, preferably chlorine, or an alkoxy or alkoxycarbonyloxy residue.

Alternatively, X can be the hydroxy group, in which case the reaction will be carried out in the presence of agents such as N'-dicyclohexyl-carbodiimide or carbonyldiimidazole.

The following example illustrates the process of the invention.

EXAMPLE 2.34 g of N-acetylglycine (0.02 mole) are dissolved in 200 ml of a mixture of 1:1 toluene-chloroform and 2.8 ml of triethylamine (0.02 mole+5%). The mixture is cooled to 0° C., then 2.6 ml of isobutyl chloroformate (0.02 mole ) are added, with stirring, keeping temperature below 5° C., to form the mixed anhydride. After 10 minutes, a solution of 3.80 g of 5-methoxytryptamine (0.02 mole ) in 80 ml of chloroform, cooled at 0° C., is added.

The mixture is stirred at room temperature for 20 hours, the precipitate is pump filtered, washing with 10% HCl, then with water. The precipitate is dissolved in acetone, dried over sodium sulfate and solvent is evaporated off under reduced pressure. The residue is recrystallized from isopropyl ether/isopropyl alcohol, to obtain 2.2 g of amide (I).

The obtained compound melts at 138°–140° C.; it is soluble in alcohols and ketones, poorly soluble in water. The structure of the compound is confirmed by the elementary analysis, as well as by the $^1$H-NMR spectrum.

| p.p.m. | integration | multiplicity | assignment |
|---|---|---|---|
| 1.95 | 3H | singlet | $CH_3CO$ |
| 2.82 | 2H | triplet J = 7Hz | $CH_2C=$ |
| 3.3–3.6 | 2H | multiplet, triplet after deuter. | $CH_2CH_2NH$ |
| 3.72 | 2H | doublet J = 7Hz, singlet after deuter. | $CH_2CO$ |
| 3.83 | 3H | singlet | $CH_3O$ |
| 6.7–7.3 | 4H | multiplet | aromatici |
| 7.9 | 1H | triplet J = 7Hz, it disappears upon deuter. | NHCO |
| 8.12 | 1H | triplet J = 7Hz, it disappears upon deuter. | NHCO |
| 10.65 | 1H | broad singlet it disappears upon deuter. | NH |

The present invention further relates to pharmaceutical compositions containing compound YS-2051, optionally together with conventional additives, excipients and adjuvants. Examples of said formulations are capsules, tablets, granulates containing 10 to 100 mg of YS-2051 per unit dose, or 1–10% solutions or suspensions of the active ingredient.

We claim:

1. N-[N'-acetyl(glycinyl)]-5-methoxytryptamine, of formula (I)

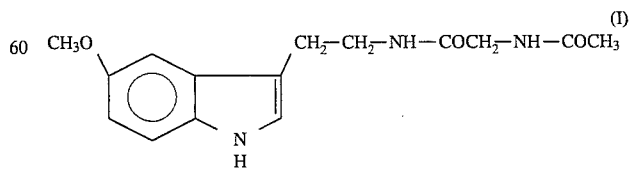

2. A process for the preparation of compound (I) of formula

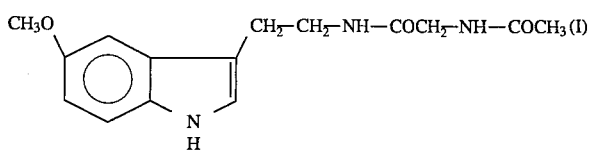

which comprises the step of an reacting N-acetyl glycine reactive derivative of formula III

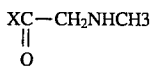   III wherein X is halogen or alcoxy or alcoxycarbonyloxy with 5-methoxy-tryptamine of formula II

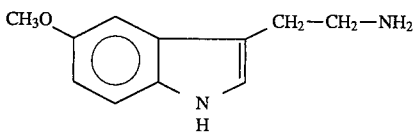   II to obtain a precipitate and purifying said precipitate by recrystallization to obtain said compound of formula (I).

3. The process according to claim 2 wherein 5-methoxytryptamine is dissolved in chloroform, the solution is added to a solution of said compound of formula III, to obtain a mixture, said mixture is stirred at room temperature for 20 hours, to obtain a precipitate, said precipitate is filtered, washed with water, dissolved in acetone, the solution is dried over sodium sulfate, the acetone evaporated under vacuo and the residue recrystallized from a mixture of isopropyl ether and isopropyl alcohol to obtain compound I.

4. A pharmaceutical composition in the from of a capsule, a tablet or a granulate having prolonged immunostimulating activity containing 10–100 mgs. compound (I) of the formula:

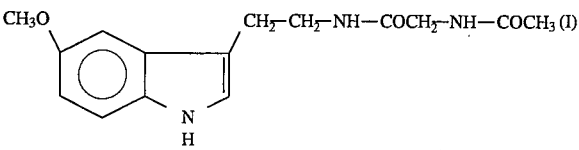

as the active ingredient per unit dose, or in the form of a solution or suspension containing 1–10% of said compound (I).

5. A method of stimulating the immune system of a patient in need thereof which comprises administering to said patient an effective amount of N-[N'-acetyl(glycinyl]-5-methoxytryptamine, of formula (1)

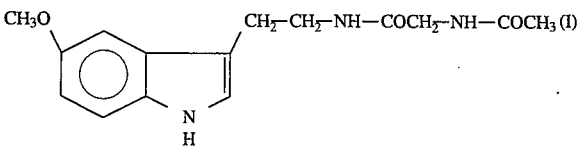

* * * * *